US00PP10494P

United States Patent [19]

Creedon

[11] Patent Number: Plant 10,494

[45] Date of Patent: Jul. 14, 1998

[54] LILIUM NAMED 'MONTREUX, ALBA'

[76] Inventor: John Creedon, P.O. Box 608, Bantam, Conn. 06750

[21] Appl. No.: 798,084

[22] Filed: Feb. 12, 1997

[51] Int. Cl.[6] ..... A01H 5/00

[52] U.S. Cl. ..... Plt./87.4

[58] Field of Search ..... Plt./87.4

*Primary Examiner*—Elizabeth C. Kemmerer

[57] ABSTRACT

An all white clone of the known Asiatic lily cultivar 'Montreux'. The new white clone has creamy "off white" color tepalage with a blush of pink in the nectary zone of the tepals. 'Montreux, alba' bears upright flowers from a tightly formed racemose inflorescence (meaning there is often only a few cm between first and second flower pedicel.) The secondary flowers are in a more loose formation. The bud shape and flower form are identical to the parent plant 'Montreux'. The white clone should be particularly valuable because of its superior stem strength and bud retention during the winter months under natural light conditions in greenhouse forced production. By comparison, there are few or no white Asiatics that will perform well in the darker months without the addition of high intensity discharge lighting to prevent bud abortion. Like its parent, 'Montreux, alba' exhibits excellent long bud form, thick petals and good vase life as a cut flower. It is particularly good for sleeving and shipping because the pedicels are non-brittle. The flowers sit flat when opened compared to other varieties and do not recurve which is often a sign of perishability. The new variety bears all the positive propagation characteristics of its parent, not the least of which is the ability to produce a relatively high bud count from a comparatively small (10–12 cm or 12–14 cm) bulb. The parent plant, 'Montreux', because of its qualities of bud count, virus and insect resistance, has been in commercial cultivation for years. The bulbs are significantly whitish in appearance, more so than 'Montreaux', and are suitable for precooling for greenhouse forced cut flower production. The variety displays good overall vigor and will force in nine (summer) to twelve (fall, winter, and spring) weeks under average to greenhouse conditions. The longest forcing time is 14 weeks under low light and cool 55F conditions. The variety displays good overall excellence of form, color, and habit.

1 Drawing Sheet

BACKGROUND OF THE INVENTION

This sport was first discovered as a severed cut flower in the greenhouses at Connecticut Cut Flower at 40 Vanderpoel Avenue, Bantam Conn. 06750 in February of 1989. It occurred as a white sport among a block of 400 pink Montreaux lilies.

The embryo of the severed stem was sent off to a tissue culture lab where it was replicated and returned to Connecticut Cut Flower for further forcing.

Upon first blooming numerous of the tissue culture bulbs had reverted to the original pink Montreux parent. This helped to confirm that we were not propagating an already known commercial variety that had occurred as a rogue among a batch of Montreux bulbs.

By rogueing out the reverted bulbs and working with the stable ones, we isolated a block that will produce the mutation consistently.

Successive generations produced by bulb scale propagation and by natural propagation from bulblets in Bantam, Conn. have demonstrated that the novel and distinctive characteristics of my new variety are fixed and hold true under asexual propagation from generation to generation.

The variety generously produces axillary bulbils when flowers have been severed and these also maybe used as propagules.

The applicant is also inter-breeding the white Montreux with other varieties now in the hope of producing a purer white of similar characteristics for later patenting.

DESCRIPTION OF THE DRAWING

Accompanying photographs have been provided showing the pink blush at the base of the white tepalage which may vary slightly in degree from bulb to bulb or fade in degree as successive flowers open on a plant from the same bulb.

The first two flowers to open will show a greater degree of pink blush.

DESCRIPTION OF THE NEW VARIETY

The following is a detailed description of my new variety of Asiatic hybrid lily with nomenclature according to the International Lily Register of The Royal Horticultural Society of London, England, Third Edition, 1982, compiled by A. C. Leslie, and with color designation according to the R.H.S. of London Colour Chart, first published by The Royal Horticultural Society in 1966 in association with the Flower Council of Holland in Leiden.

The Plant

An average of 10 representative plants was used to obtain the statistical data obtained below.

Origin: Sport.

Parentage: Montreux sport.

Classification:

*Horticultural.*—Upright Asiatic Hybrid Lily, Division I-A according to the International Lily Register of Royal Horticultural Society of London, England, third Edition, 1982, compiled by A. C. Leslie.

Form: Single stem, tall, erect and stately.

Height: Average is 93.4 cm. On stems produced under greenhouse forcing conditions from bulbs of about 12–14 cm. in circumference with adequate light levels (early Spring forcing at 58 degrees F.).

Growth: Vigorous and upright.

Foliage:

*Quantity.*—Abundant.

*Leaf size.*—Averaging 1.13 cm. in width and 9.9 cm. in length.

*Leaf shape.*—Lanceolate with acumiante tip.

*Texture.*—Leathery.
*Aspect.*—Glossy with minimal pubescence.
*Color.*—Dark green, lighter on the lower side.

The Bud

Form: Long ovoid and obtuse.
Size: Average 7.8 cm. in length and 6.75 cm. In circumference.
Opening rate: The buds open slowly, usually one flower on the first day, and successive flowers the following day.
Color: Yellow-white RHC 158A, yellow RHC 8D, and yellow RHC 11D are the closest matching colors. See attached research by Dr. Richard McAvoy, University of Connecticut.
Peduncle:
*Length.*—Average 9.1 cm.
*Color.*—Dark green.

The Flower

Blooming habit: Once annually, outdoor habit has not yet been observed.
Size: The flowers are medium sized, averaging 14.5 cm. In diameter.
Borne: As a single tightly formed racemose (meaning there is often only a few cm. Between first and second flower pedical.) The secondary flowers are in a more loose formation. The shape and flower form are identical to the parent plant. Montreux, producing 5–7 buds from a 12–14 cm. bulb.
Shape: Flowers open flat with little recurving on successive days.
Tepalage:
*Number.*—Six.
*Length.*—Average 8.1 cm. Width average 2.9 cm.
*Arrangement.*—Hexagonal and imbricated.
*Shape.*—Ovate with entire margins and with an acute tip.
*Appearance.*—Not glossy.
*Color.*—The base color is white—most closely matched by RHC 158A, RHC 11D and RHC 8 D. The lack of a broad selection of white color chips is a hindrance in the identification. The blush area (extends about 2 cm. from the nectaries and most closely resembles Red RHC 36A and 36 B on the samples we observed.
*Tepal spotting.*—The basal third of each tepal is marked with inconspicuous deep maroon spots, extending just above the nectaries. These spots extend up to 1 cm beyond the nectaries.
*Tepal longevity.*—The tepals stay on the stem in good condition for 7 days summer, and 10–14 days winter. Outdoor conditions have not been observed.
*Pedicel.*—Length: Average 7.6 cm. Form: Sturdy and ascending up to 4 degrees from the horizontal. Color: Dark green.
*Fragance.*—None.
*Disease resistance.*—The variety is resistant to virus and aphids.
*Lasting quality.*—Flowers are long lasting both on the plant and as cut flower.

The Reproductive Organs

Stamens:
*Number.*—Six.
*Length.*—Average 6.0 cm.
*Arrangement.*—Typical of the genus Lillium.
*Anthers.*—Length average 1.1 cm.
Pollen:
*Color.*—At the closed stage of anther development the color most closely resembled Brown RHC 200C, Brown RHC 200D and Brown RHC 200B. At the open stage of anther development the color also resembled Grayed-Orange RHC 165 A, as well as Brown RHC 200B and Brown RHC 200A.
*Filaments.*—Length: Averge 6.0 cm. Color: White.
Pistils:
*Number.*—One.
*Length.*—Average 5.6 cm.
Stigma:
*Size.*—Average 4.48 cm.
*Color.*—Pale green.
*Style.*—Size: 4.4 mm. Color: Soft brown on green background.
Character of ovary: Typical of genus Lillium.
*Fertility.*—The fruit is fertile.
*Shape.*—Ovoid.
*Immature color.*—Green.
*Color at maturity.*—Soft brown to tan.

Comparison of the color of the oriental hybrid lily cultivar 'Montreaux' to two samples of a 'Montreaux, alba' sport The lily cultivar Montreaux has a tepal basal color that lied between the greyed-purple and greyed-red groups of The Royal Horticultural Society Colour Chart (see Tables below). CIELAB cordinates show Montreaux to have a basal hue angle of 9.445, with a chroma of 31.99 and a L-value of 56.38. The tepals of Montreaux have a blush color between the greyed-purple and red groups of the RHC chart. The CIELAB calculated hue angle of the blush is similar to the basal hue angle but the L-value is lower and the chroma is higher.

Two samples of the sport 'Montreaux, alba' have a significantly different basal and blush color from 'Montreaux'. These selections—samples 1 and 2—have a basal color between the RHC yellow-white and yellow groups (see tables below). The CIELAB hue angle ranges from 97.73 to 101.9 for these samples, and the chromas range from 18.81 to 19.63, and the L-values range from 86.79 to 87.67.

The blush color of the 'Montreaux, alba' sport is closest to the RHC orange and red groups. The two samples are essentially identical to each other. Unlike 'Montreaux', the hue angle of the blush on this sport is greatly different from the basal color.

The anthers of the two samples of the 'Montreaux, alba' sport are both similar in color. The RHC color is in the brown group for closed anthers and between the greyed-orange and brown groups for open anthers. The anthers of these samples were dark, displaying a relatively low chroma and L-value.

TABLE 1

L-Value, Hue angle and Chroma for the basal color and blush of tepals from the oriental lily cultivar 'Montreaux' and two samples of a *'Montreaux, alba'* sport. (values in parentheses represent standard error of the mean).

| Cultivar or Sport | L-Value | Hue angle (H°) | Chroma (C*) |
|---|---|---|---|
| Tepal Basal Color | | | |
| Montreaux | 56.38 (0.93) | 9.445 (1.36) | 31.99 (1.06) |
| *Montreaux Alba* Sample 1 | 87.67 (0.45) | 101.9 (0.67) | 19.63 (0.22) |
| *Montreaux Alba* Sample 2 | 86.79 (0.55) | 97.73 (1.48) | 18.81 (0.36) |
| Tepal Blush Color | | | |
| Montreaux | 50.18 (0.66) | 10.73 (0.70) | 43.6 (2.23) |
| *Montreaux Alba* Sample 1 | 78.89 (0.68) | 68.02 (1.86) | 19.53 (0.35) |
| *Montreaux Alba* Sample 2 | 78.06 (0.67) | 62.85 (2.23) | 19.77 (0.36) |
| Athers of *Montreaux Alba* selections | | | |
| Opened | 30.34 (0.81) | 30.51 (3.48) | 13.42 (0.58) |
| Closed | 36.4 (0.20) | 45.60 (0.68) | 14.19 (0.31) |

TABLE 2

Color comparison of the cultivar Montreaux to two samples of a Montreaux alba sport using ΔE, ΔHue, and L-value, and Chroma differences.

| Montreaux | Tepal basal color | | | | Tepal blush color | | | |
|---|---|---|---|---|---|---|---|---|
| Alba selection | ΔE | L diff. | Δ Hue | C* diff. | ΔE | L diff. | Δ Hue | C* diff. |
| Sample 1 | 49.42 | −31.3 | −36.21 | 12.36 | 46.76 | −28.7 | −27.98 | 24.07 |
| Sample 2 | 47.6 | −30.4 | −34.17 | 13.16 | 44.84 | −27.9 | −25.79 | 23.83 |

TABLE 3

Comparison of the basal color of the cultivar Montreaux and two samples of a Montreaux alba sport with the Royal Horticultural Society Colour Chart standards using ΔE, ΔH°, and the difference L-value and Chroma differences.

| Cultivar or sport | Closest matching color group and RHS color chip | RHS chip values L-Value | Hue angle | Chroma |
|---|---|---|---|---|
| Montreaux | Greyed-Purple RHC 185D | 56.4 | 5.73 | 37.1 |
| | Greyed-Red RHC 181C | 53 | 22.16 | 35.5 |
| | Greyed-Purple RHC 184D | 48.9 | 10.21 | 37.8 |
| Montreaux | Yellow-White RHC 158A | 89.2 | 93.64 | 22.04 |
| Alba | Yellow RHC 11D | 94.2 | 99.87 | 18.68 |
| Sample 1 | Yellow 8D | 94 | 101.9 | 23.2 |
| Montreaux | Yellow-White RHC 158A | 89.2 | 93.64 | 22.04 |
| Alba | Yellow RHC 11D | 94.2 | 99.87 | 18.68 |
| Sample 2 | Yellow RHC 8D | 94 | 101.9 | 23.2 |

| Cultivar or sport | Closest matching color group and RHS color chip | Lily color v. RHS color chip differences ΔE-value | L-value | ΔHue angle | Chroma |
|---|---|---|---|---|---|
| Montreaux | Greyed-Purple RHC 185D | 5.56 | −0.02 | 2.2352 | −5.09 |
| | Greyed-Red RHC 181C | 8.92 | 3.38 | −7.467 | −3.53 |
| | Greyed-Purple RHC 184D | 9.48 | 7.48 | −0.464 | −5.8 |
| Montreaux | Yellow-White RHC 158A | 4.147 | −1.53 | 3.0085 | −2.41 |
| Alba | Yellow RHC 11D | 6.636 | −6.53 | 0.6911 | 0.958 |
| Sample 1 | Yellow 8D | 7.286 | −6.33 | −0.002 | −3.57 |

TABLE 3-continued

Comparison of the basal color of the cultivar Montreaux and two samples of a Montreaux alba sport with the Royal Horticultural Society Colour Chart standards using ΔE, ΔH°, and the difference L-value and Chroma differences.

| | | | | | |
|---|---|---|---|---|---|
| Montreaux | Yellow-White RHC 158A | 4.287 | −2.41 | 1.4527 | −3.23 |
| Alba | Yellow RHC 11D | 7.444 | −7.41 | −0.699 | 0.135 |
| Sample 2 | Yellow RHC 8D | 8.58 | −7.21 | −1.535 | −4.39 |

TABLE 4

Comparison of the tepal blush color of the cultivar Montreaux and two samples of a Montreaux alba sport with the Royal Horticultural Society Colour Chart standards using ΔE, ΔH°, and the difference L-value and Chroma differences.

| Cultivar or sport | Closest matching color group and RHS color chip | RHS chip values L-Value | Hue angle | Chroma |
|---|---|---|---|---|
| Montreaux | Greyed-Purple RHC 184D | 48.9 | 10.21 | 37.8 |
| | Greyed-Purple RHC 185C | 47.9 | 10.1 | 37.07 |
| | Red RHC 54A | 54.4 | 9.5 | 50.29 |
| Montreaux | Red RHC 36B | 85.3 | 47.06 | 15.71 |
| Alba | Red RHC 36A | 84.4 | 45.36 | 22.49 |
| Sample 1 | Orange 27A | 88.1 | 70.36 | 24.1 |
| Montreaux | Red RHC 36A | 84.4 | 45.36 | 22.49 |
| Alba | Red RHC 36B | 85.3 | 47.06 | 15.71 |
| Sample 2 | Orange RHC 29D | 89 | 61.06 | 19.43 |

| Cultivar or sport | Closest matching color group and RHS color chip | Lily color v. RHS color chip differences ΔE-value | L-value | ΔHue angle | Chroma |
|---|---|---|---|---|---|
| Montreaux | Greyed-Purple RHC 184D | 5.955 | 1.28 | 0.3704 | 5.804 |
| | Greyed-Purple RHC 185C | 6.93 | 2.28 | 0.4457 | 6.529 |
| | Red RHC 54A | 7.971 | −4.22 | 1.0076 | −6.69 |
| Montreaux | Red RHC 36B | 9.812 | −6.41 | 6.3701 | 3.822 |
| Alba | Red RHC 36A | 10.26 | −5.51 | 8.2335 | −2.96 |
| Sample 1 | Orange 27A | 10.32 | −9.21 | −0.887 | −4.57 |
| Montreaux | Red RHC 36A | 9.346 | −6.34 | 6.4114 | −2.72 |
| Alba | Red RHC 36B | 9.609 | −7.24 | 4.84002 | 4.06 |
| Sample 2 | Orange RHC 29D | 10.96 | −10.9 | 0.6127 | 0.342 |

TABLE 5

Comparison of the anther color of a Montreaux alba sport with the Royal Horticultural Society Colour Chart standards using ΔE, ΔH°, and the difference L-value and Chroma differences.

| Stage of Anther development | Closest matching color group and RHS color chip | RHS chip values L-Value | Hue angle | Chroma |
|---|---|---|---|---|
| Opened | Brown RHC 200B | 33.2 | 39.523 | 10.37 |
| | Greyed-Orange RHC 165A | 40.4 | 49.022 | 18.15 |
| | Brown RHC 200A | 30.2 | 26.928 | 7.066 |
| Closed | Brown RHC 200C | 35.6 | 47.49 | 11.4 |
| | Brown RHC 200D | 40 | 50.29 | 16.12 |
| | Brown RHC 200B | 33.2 | 39.52 | 10.37 |

| Stage of Anther development | Closest matching color group and RHS color chip | Lily color v. RHS color chip differences ΔE-value | L-value | ΔHue angle | Chroma |
|---|---|---|---|---|---|
| Opened | Brown RHC 200B | 4.466 | −2.86 | −1.748 | 2.951 |
| | Greyed-Orange RHC 165A | 5.691 | −10.1 | −4.872 | −4.82 |
| | Brown RHC 200A | 6.295 | 0.14 | 0.6883 | 6.256 |

TABLE 5-continued

Comparison of the anther color of a Montreaux alba sport with the Royal Horticultural Society Colour Chart standards using ΔE, ΔH°, and the difference L-value and Chroma differences.

| | | | | | |
|---|---|---|---|---|---|
| Closed | Brown RHC 200C | 2.942 | 0.83 | −0.426 | 2.79 |
| | Brown RHC 200D | 4.247 | −3.57 | −1.244 | −1.93 |
| | Brown RHC 200B | 5.129 | 3.23 | 1.2799 | 3.814 |

This new lily variety most closely resembles the variety 'Montreaux' in every way except that it is white, with a pink blush reminiscent of its parentage displayed in the zone of the nectaries, and most evident on the first two flowers that open. The bulb is more notably white in appearance.

I claim:

1. A new distinctive Asiatic hybrid lily plant, as shown herein and described containing valuable characteristics of stem strength and bud retenton, particularly for a white lily to be forced under greenhouse conditions of reduced light during winter months, without the aid of high intensity discharge (HID) lighting.

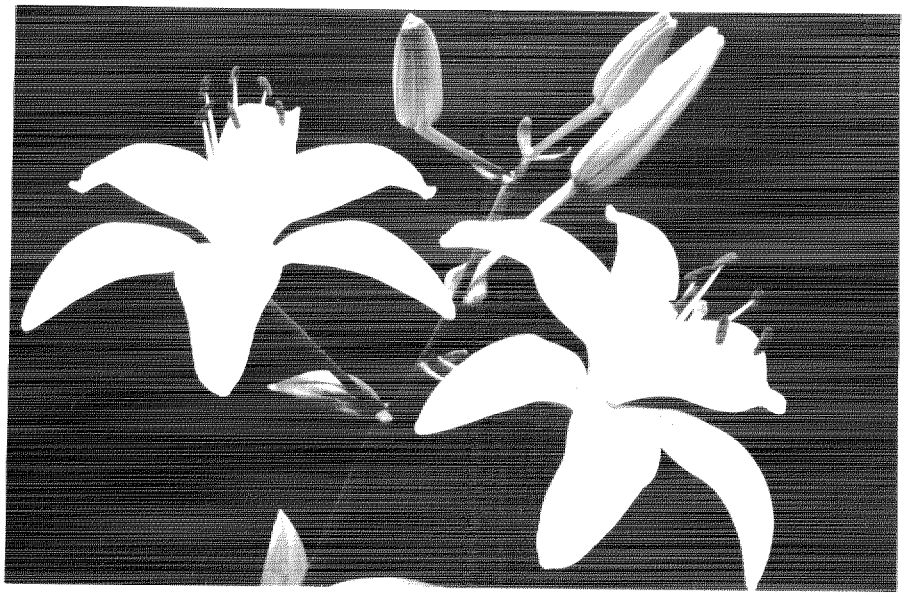
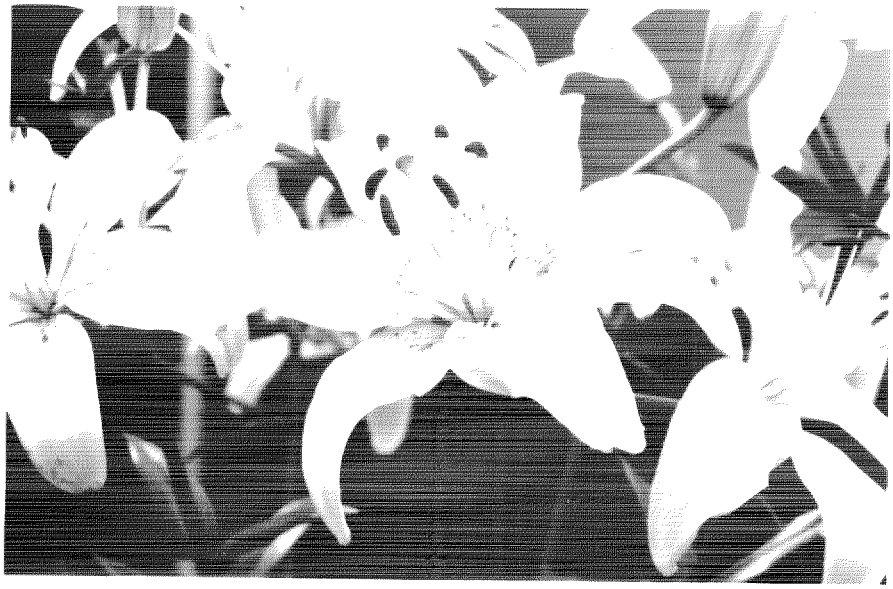

* * * * *